United States Patent
Seltzer et al.

(10) Patent No.: US 10,163,176 B2
(45) Date of Patent: Dec. 25, 2018

(54) CLOSED LOOP WORKFLOW

(75) Inventors: Paul Seltzer, Monsey, NY (US); Paul J. Chang, Chicago, IL (US)

(73) Assignees: KONINKLIJKE PHILIPS N.V., Eindhoven (NL); THE UNIVERSITY OF CHICAGO, Chicago, IL (US)

( * ) Notice: Subject to any disclaimer, the term of this patent is extended or adjusted under 35 U.S.C. 154(b) by 442 days.

(21) Appl. No.: 13/378,054

(22) PCT Filed: Jun. 16, 2010

(86) PCT No.: PCT/IB2010/052715
§ 371 (c)(1),
(2), (4) Date: Dec. 14, 2011

(87) PCT Pub. No.: WO2011/001319
PCT Pub. Date: Jan. 6, 2011

(65) Prior Publication Data
US 2012/0109682 A1    May 3, 2012

Related U.S. Application Data

(60) Provisional application No. 61/222,132, filed on Jul. 1, 2009, provisional application No. 61/263,054, filed on Nov. 20, 2009.

(51) Int. Cl.
G06Q 50/22     (2018.01)
G06Q 10/06     (2012.01)
G16H 40/20     (2018.01)

(52) U.S. Cl.
CPC ........... *G06Q 50/22* (2013.01); *G06Q 10/06* (2013.01); *G16H 40/20* (2018.01)

(58) Field of Classification Search
CPC ........ G06Q 50/22–50/24; G06Q 10/06; G16H 40/20
USPC .......................................................... 705/2–3
See application file for complete search history.

(56) References Cited

U.S. PATENT DOCUMENTS

| | | | |
|---|---|---|---|
| 7,562,026 B2 | 7/2009 | DelMonego et al. | |
| 2002/0099571 A1 | 7/2002 | Waku et al. | |
| 2003/0149597 A1* | 8/2003 | Zaleski ............................. | 705/2 |
| 2003/0212580 A1* | 11/2003 | Shen ...................... | G06Q 10/10 705/2 |
| 2006/0020209 A1* | 1/2006 | Hashimoto ................... | 600/458 |
| 2006/0109961 A1 | 5/2006 | Mahesh et al. | |
| 2006/0173713 A1 | 8/2006 | Petro et al. | |
| 2006/0184943 A1* | 8/2006 | DelMonego et al. ........ | 718/100 |
| 2006/0265253 A1* | 11/2006 | Rao et al. ........................ | 705/3 |
| 2007/0027459 A1* | 2/2007 | Horvath .............. | G06F 19/3412 606/147 |
| 2007/0049815 A1 | 3/2007 | Sanjay-Gopal et al. | |
| 2007/0109294 A1 | 5/2007 | Gotman et al. | |
| 2008/0091473 A1 | 4/2008 | Choppin | |

(Continued)

FOREIGN PATENT DOCUMENTS

| | | |
|---|---|---|
| JP | 7253963 A | 10/1995 |
| JP | 2004318570 | 11/2004 |

(Continued)

*Primary Examiner* — Robert A Sorey

(57) ABSTRACT

A system includes an orchestrator (114) with a processor (116) and a plurality of processing actors (102) in communication therewith. The processor (116) orchestrates closed-loop implementation of a healthcare imaging workflow plan by the plurality of processing actors (102).

23 Claims, 4 Drawing Sheets

(56) References Cited

U.S. PATENT DOCUMENTS

| | | | |
|---|---|---|---|
| 2008/0126126 A1* | 5/2008 | Ballai | G06Q 10/06 705/2 |
| 2008/0312959 A1* | 12/2008 | Rose et al. | 705/2 |
| 2009/0099863 A1* | 4/2009 | Einav et al. | 705/2 |
| 2009/0132586 A1 | 5/2009 | Napora et al. | |
| 2009/0132636 A1* | 5/2009 | Natanzon et al. | 709/201 |
| 2009/0138318 A1* | 5/2009 | Hawkins et al. | 705/9 |
| 2009/0287500 A1* | 11/2009 | Benjamin et al. | 705/2 |
| 2010/0042653 A1* | 2/2010 | Krishnan et al. | 707/104.1 |
| 2010/0099974 A1* | 4/2010 | Desai | 600/411 |
| 2012/0065987 A1* | 3/2012 | Farooq | G06F 19/328 705/2 |
| 2013/0066646 A1* | 3/2013 | Backhaus | G06F 19/327 705/2 |

FOREIGN PATENT DOCUMENTS

| | | |
|---|---|---|
| JP | 2005020188 | 1/2005 |
| JP | 2007190183 | 8/2007 |
| JP | 2007234811 | 9/2007 |
| JP | 2008245789 | 10/2008 |
| JP | 2009134424 A | 6/2009 |

* cited by examiner

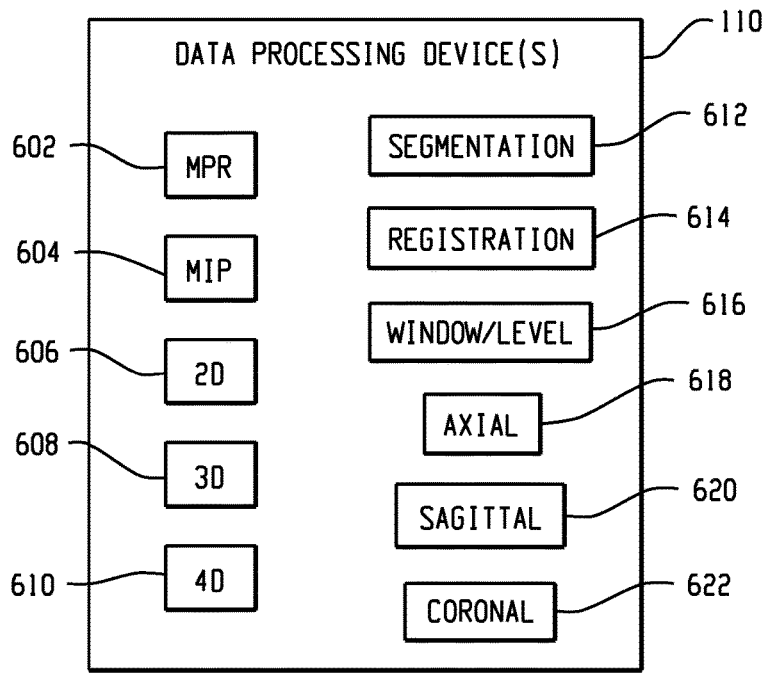
Fig. 6
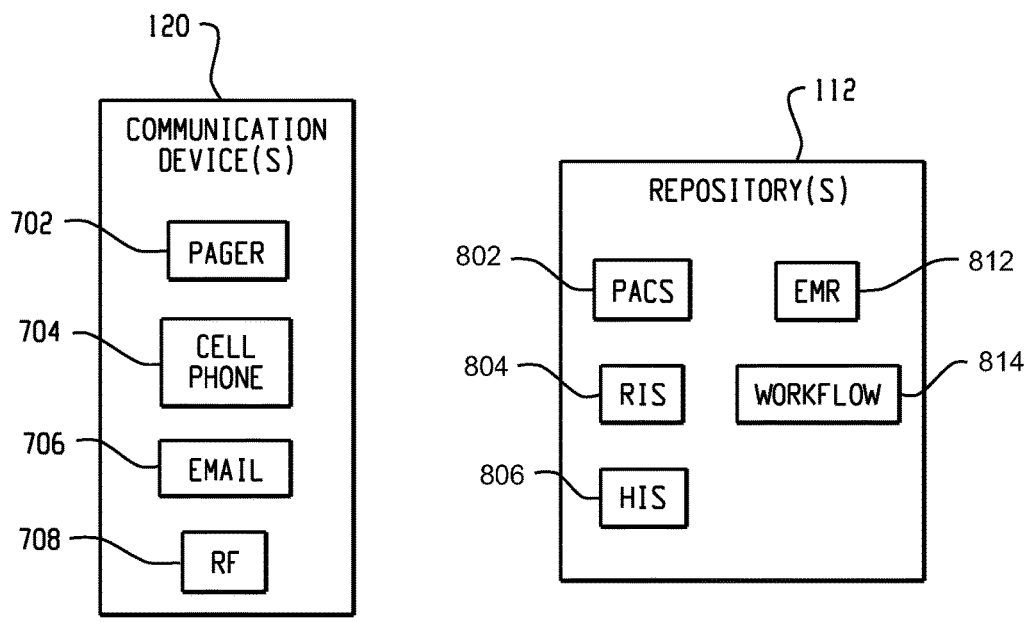
Fig. 7
Fig. 8

CLOSED LOOP WORKFLOW

CROSS REFERENCE TO RELATED APPLICATIONS

This application claims the benefit of U.S. provisional application Ser. No. 61/222,132 filed Jul. 1, 2009 and U.S. provisional application Ser. No. 61/263,054 filed Nov. 20, 2009, both of which are incorporated herein by reference.

DESCRIPTION

The following generally relates to healthcare workflow and is described with particular application to imaging workflow; however, it is also amenable to other healthcare workflow applications and to non-healthcare applications.

Generally, the process for medical imaging starts when a clinician decides that a patient should be imaged to facilitate answering a clinical question about the patient and ends once the imaging results are communicated to the clinician. The process can be broken down from initial scheduling by clinician, pre-imaging procedure preparation, imaging suite preparation, post procedure preparation, report generation by a radiologist, and forwarding of the report to the clinician. The foregoing process can be complex, involving multiple people and non-integrated computer systems that must be choreographed into harmonization in order to achieve quality and efficiency. A contributor to the complexity is the amount of communication between people and computer systems.

Examples of communication by personnel include: filling out and submitting requests for patient information; determining the imaging procedure by the referring clinician and communicating the "clinical question" to the radiologist; scheduling the imaging exam; checking the patient in for the exam; determining suitable processing of the imaging results; following up with referring clinician, etc. Examples of communication with computing systems include requesting information from a hospital information system (HIS); providing scheduling information to a radiology information system (RIS); providing examination information to the billing department; configuring an imaging system for scanning; performing the scan; storing and viewing imaging data in a picture archiving and communication system (PACS), etc.

The complexity of the above-noted communication may result in inefficiently using healthcare personnel (e.g., personnel entering data, filing out and submitting requests for information, etc.), unnecessarily consuming patient time (e.g., having the patient wait while personnel retrieve and enter information and set up equipment, etc.), selecting an imaging procedure without some relevant patient information (e.g., due to the difficulty in obtaining information, non-compatible electronic format, unknown data, etc.), tracking implementation of workflow, etc.

Aspects of the present application address the above-referenced matters and others.

According to one aspect, a system includes an orchestrator with a processor and a plurality of processing actors in communication therewith. The processor orchestrates closed-loop implementation of a healthcare imaging workflow plan by the plurality of processing actors.

In another embodiment, a method includes implementing a healthcare workflow plan for a patient via a processor of an orchestrator in communication with a plurality of processing actors that process sub-portions of the workflow plan via closed-loop orchestration.

In another embodiment, a computer readable storage medium with computer executable instructions, which, when executed by a processor of a computer, cause the computer to orchestrate implementation of a healthcare imaging workflow plan with a plurality of workflow processing actors.

The invention may take form in various components and arrangements of components, and in various steps and arrangements of steps. The drawings are only for purposes of illustrating the preferred embodiments and are not to be construed as limiting the invention.

FIG. 6 illustrates an example data processing device(s).

FIG. 7 illustrates an example communication device(s).

FIG. 8 illustrates an example repository(s).

The following describes closed-loop workflow in connection with an imaging application. In this context, closed-loop workflow generally relates to computing system orchestration of events (and changes, additions and deletions thereto) that occur from about the point in time at which an imaging procedure is prescribed until at least the imaging procedure is performed. The workflow may further extend until the report of the findings from the image data from the procedure is generated and/or conveyed to the appropriate physician. Although described below in connection with an imaging application, it is to be appreciated that closed-loop workflow can also be employed in connection with other applications.

Figure 1:
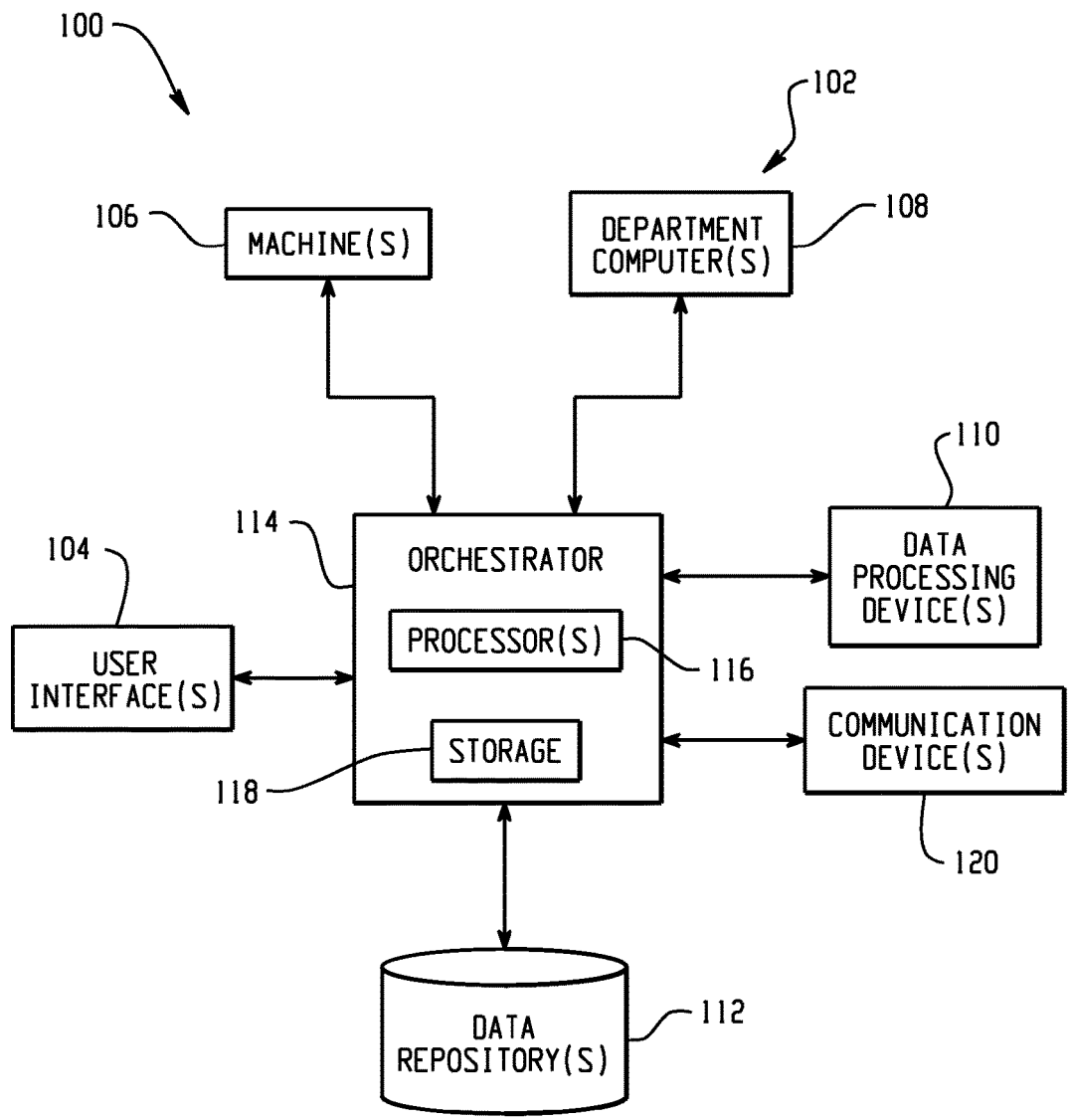
FIG. 1 illustrates an example system including an orchestrator for orchestrating workflow via a plurality of actors.

FIG. 1 illustrates an example system 100 with a plurality of processing components actors 102 that contribute to the implementation of a workflow.

The actors 102 include one or more user interfaces 104, which, at least, receive input corresponding to the workflow from a user. The one or more user interfaces 104 may include web, console, mobile phone, and/or other applications, executed by a processor(s), and including graphical and/or command line interfaces. The actors 102 also include one or more machines 106, which obtain and/or process information related to the workflow. At least one of the machines 106 may be hardware and/or software based.

The actors 102 further include one or more department computing devices 108. Examples of such a device 108 include the computer in a billing department that stores patient billing information associated with the workflow, the computer in an admitting department that stores patient information associated with the workflow, the computer in a laboratory department that stores patient laboratory information associated with the workflow, etc.

The actors 102 further include one or more data processing devices 110 that process data from one or more other actors 102 and/or provide processed data to one or more of the other actors 102. The actors 102 further include a data repository 112 that stores information used by and/or provided by the one or more of the other actors 102. The data repository 112 can be a single data storage device or a plurality of data storage devices, including distributed data storage.

The actors further include an orchestrator 114 that orchestrates implementation of a workflow via one or more of the other actors 102. The orchestrator 114 may include one or more processors 116 and computer readable storage medium (storage) 118 for storing computer executable instructions. The orchestrator 114 can be centralized or distributed across multiple platforms. The illustrated orchestrator 114 is also configured to communicate with one or more communication devices 120 such as a pager, a cell phone, a radio frequency identification (RFID) tag, email, a text message, an instant message, and/or other communications.

It is to be appreciated that in one instance, using the orchestrator 114 to orchestrate workflow implementation via the actors 102 allows for mitigating workflow implementation inefficiencies, improving workflow quality, and/or increasing actor interoperability, relative to a configuration in which the orchestrator 114 is omitted. By way of non-limiting example, in one instance where the orchestrator 114 is omitted, at least two of the actors 102 lack connectivity with each other, and a human or other intermediary manually transfers information between the two actors 102, which consumes times and is subject to introducing error in the transfer of the information.

Figure 9:
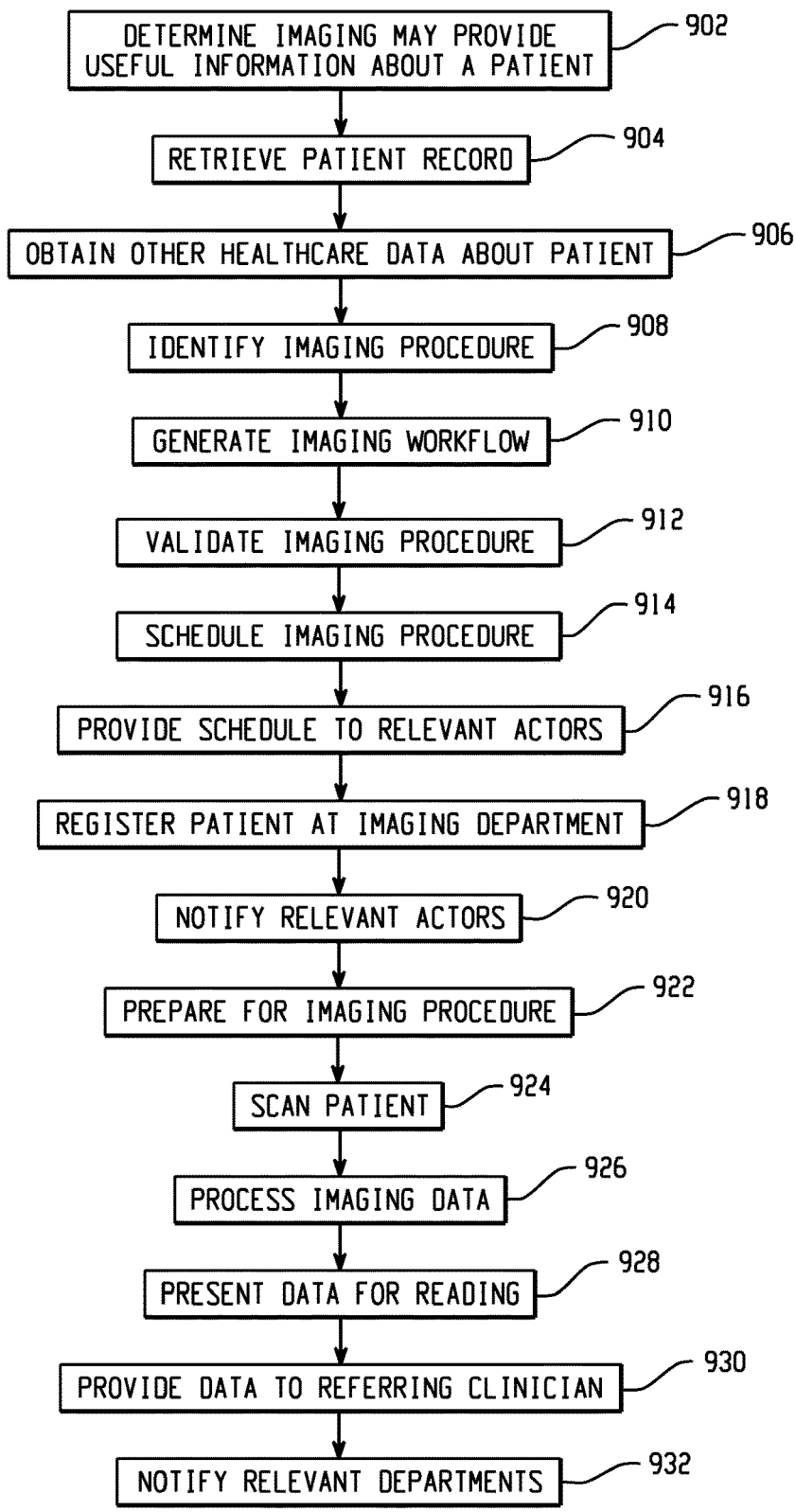
FIG. 9 illustrates example workflow.

Turning first to FIG. 9, example workflow employing the system 100 of FIG. 1 is illustrated. This example is described in the context of a healthcare imaging workflow for sake of brevity and clarity, and is not limiting. However, other workflows, including non-healthcare imaging application and/or non-healthcare applications are contemplated herein. In addition, the acts and the ordering of the acts are not limiting. As such, other embodiments may include more or less and/or similar or difference acts, and one or more of the acts may occur in a different order.

At 902, it is determined that an imaging procedure may provide useful information with respect to a patient. For example, it may be determined that imaging data may facilitate diagnosing, or answering a clinical question about, the patient. This decision may be rendered based on various information such as, but not limited to, findings from imaging, laboratory and/or health related information, a diagnosis, patient history, genetics, etc. In addition, the imaging procedure may be a first imaging procedure for a new imaging workflow or part of or an extension to an existing workflow.

At 904, a patient record for the patient is retrieved, for example, from the data repository 112 via the orchestrator 114. An example patient record may include demographic information, patient history, family history, a list of previous medical procedures scheduled and/or performed, results of previous medical procedures (e.g., imaging procedure and non-imaging procedures), whether the patient has been a patient at the particular healthcare facility, etc. If no record exists, then a patient record can be created for the patient.

At 906, other healthcare information about the patient is obtained from the data repository 112 via the orchestrator 114. Such information may include information regarding the patient's health care insurance provider (e.g., provider name, plan, deductible, deductible met, maximum coverage, co-pay, etc.), whether the patient has any outstanding bills, the patient employer, dietary information, allergies, etc. As noted herein, this information may be retrieved from various different sub-repositories employing various different communication protocols.

At 908, one or more imaging procedures for the patient is identified based at least in part on imaging and/or non-imaging healthcare information from the repository 112. One or more of the imaging procedures may include the same imaging modality and/or different imaging modalities. Examples of such modalities include, but are not limited to, CT, PET, SPECT, US, X-ray, MRI, combination scanners, etc. The particular one or more imaging procedures may be selected based on various information such as, but not limited to, patient availability, urgency of study, efficiency, image modality image, throughput, prioritization, optimization, etc. Again, the imaging data may facilitate diagnosing, or answering a clinical question about the patient.

At 910, the orchestrator 114 orchestrates generation of an imaging workflow for the imaging procedure. This may include entering a particular imaging procedure, the anatomy of interest to be scanned, and/or the clinical question via an interface 104. This information is provided to the orchestrator 114, which generates the imaging workflow plan, which generally includes the acts or events to be implemented for the imaging procedure.

The workflow can be generated based on a default workflow, a previous workflow for the patient, a workflow for another patient, and/or newly generated. The workflow may also be generated based on the health insurance provider, whether or not the patient has any outstanding invoices, etc. The workflow may also consist of multiple child workflows, be a child workflow of one or more parent workflows, be a sibling workflows with one or more other workflows. The imaging workflow can be stored in the data repository(s) 112.

At 912, the orchestrator 114 notifies the radiologist regarding the imaging workflow, and the radiologist validates the imaging procedure in the imaging workflow. By way of example, the radiologist can determine whether the identified imaging procedure is suitable for addressing the clinical question or if another imaging procedure would likely result in more useful information. If the identified plan is suitable, the radiologist confirms or validates the imaging procedure. Otherwise, the radiologist identifies an alternative plan and/or updates the workflow, or rejects the workflow. One or more additional or alternative actors (e.g., the referring physician, an on-call physician, a specialist, etc.) may likewise be notified and/or render similar types of responses. The imaging workflow can be updated to reflect that the imaging procedure has been validated or changed.

The orchestrator 114 also facilitates making any changes to the workflow before or during implementation of the workflow. Suitable changes include, but are not limited to, extending the workflow plan to include one or more additional imaging procedures (e.g., the same and/or different imaging modalities), cancelling an imaging procedure, splitting an imaging procedure into two or more imaging procedures, adding one or more non-imaging procedures such as a laboratory (e.g., blood, urine, etc.) test, a stress test, an ECG, including child workflows, adding the workflow to another workflow, etc. based on one or more of the sources noted herein and/or other sources.

At 914, the orchestrator 114 schedules the imaging procedure based at least on the availability of the patient, the availability of the scanner, and/or the availability of the radiologist. In one instance, healthcare personnel (e.g., staff at the clinician's office) interact with the orchestrator 114 to schedule the imaging procedure. For example, the healthcare personnel may enter the patient's availability or select one or more days and times when the patient is expected to be free. In another instance, the patient interacts with orchestrator 114 to schedule the procedure, for example, via a home or other computer.

The orchestrator 114 also facilitates making any changes to the schedule. Suitable changes include, but are not limited to, changes to the date and/or time based on the patient, radiology department personnel, imaging system availability and/or prioritization, information from the billing department, laboratory results, etc. The orchestrator 114 also facilitates making other changes to the workflow such as one or more of the changes noted above. The imaging workflow can be updated to reflect that the scheduled imaging procedure.

At 916, the orchestrator 114 provides the schedule, via the communication device(s) 120, to the patient, referring clinician, the radiology department, the scanner, the radiologist, and/or other relevant person. The orchestrator 114 may also be configured to send reminders to these actors when a predetermined time interval prior the imaging procedure is reached. The orchestrator 114 may also be used to communicate any changes to the scheduled procedure date or time to the relevant actors. Such changes may be due to patient findings determined after the schedule has been created, a change in available personnel and/or system resources, an intervening higher priority, etc. The orchestrator 114 further can notify the patient, the technician, the radiologist, etc. regarding any pre or post-procedure instructions (e.g., no eating after midnight, drink contrast one hour prior to procedure, lie flat after the procedure for at least 1 hr, etc.)

At 918, assuming the scheduled day has arrived, the patient registers with the imaging department for the imaging procedure. In one instance, the patient notifies imaging department personnel, and the personnel confirm the appointment and log the patient in as ready to be scanned. In another instance, the patient logs him/herself in via a registration computer console. In another instance, wireless technology is used to automatically identify the patient's presence. In this instance, the patient can be automatically registered and/or notified to confirm their registration via the wireless technology. The imaging workflow can be updated to reflect that the patient has arrived for the imaging procedure.

At 920, the orchestrator 114 notifies the technician assigned to perform the imaging procedure, the radiology department computer system, the radiologist, and the scanner that the patient has arrived. The radiology department computer system 108 may include this information in an electronic "dashboard" or mechanism used to manage the scanning and/or technician resources in the department. In instances where the patient is carrying a communications device 120 such as a pager or like, the orchestrator 114 can notify the patient about various information such as when the patient should ingest contrast, when the patient should go to the exam room, if the procedure will be delayed and by how long, and/or other pre-imaging procedure information.

In instances in which the availability of the imaging system has changed, a higher priority event occurs, a more efficient workflow has been determined, the workflow has been cancelled, a pre-procedure event has not occurred, the workflow has been interrupted by facility personnel, the imaging procedure has been delayed, the imaging system or modality has changed, etc., the orchestrator 114 facilitates the changing the workflow and/or apprising relevant parties of the change and coordinating implementation of the change workflow. The imaging workflow can be updated to reflect the current status of the imaging procedure.

At 922, the scanner is configured to perform the imaging procedure. For example, the orchestrator 114 can identify an imaging protocol for the imaging procedure to the scanner. In instances where the patient is carrying a communications device 120 such as an RFID tag, the orchestrator 114 and/or the scanner can sense when the patient is approaching the scanner and invoke the scanner at that point to load the protocol in preparation for scanning the patient. Of course, the technician can modify the protocol and/or one or more parameters. In another instance, the technician notifies the imaging system that the patient is ready to be imaged and then the imaging system automatically loads the appropriate protocol.

At 924, the patient is scanned. This includes performing one or more scans (e.g., one or multi-slice) using one or more imaging modalities. The imaging workflow can be updated to indicate that the imaging procedure has been performed. Other imaging and/or non-imaging procedures that still need to be scheduled and/or performed are still in the workflow plan.

At 926, the orchestrator 114 transfers the imaging data to the data processing device(s) 110, which processes the imaging data. The data processing device(s) processes the imaging data based on various processing algorithms including, but not limited to 2D, 3D, 4D, MIP, MPR, etc. algorithms. Additionally or alternatively, the data processing device(s) 110 processes the imaging data based on the type of scanner and/or scan. Additionally or alternatively, the data processing device(s) processes the imaging data based on predetermined preference of the radiologist reading the imaging data. The imaging workflow can be updated to indicate that the imaging data has been processed.

At 928, the orchestrator 114 employs the communication device(s) 120 to notify the radiologist that the processed imaging data is available for viewing. The orchestrator 114 can also employ the communication device(s) 120 to notify other actors regarding the availability of the imaging data. The imaging workflow can be updated to reflect the processed data is ready to be read.

At 930, the orchestrator 114 employs the communication device(s) 120 to notify the referring clinician and/or other actors that the processed imaging data and radiologist report is ready for viewing. The imaging workflow can be updated to indicate that the image data and the report are ready to be reviewed.

At 932, the orchestrator 114 communicates with various actors. For example, the orchestrator 114 can communicate with a billing department, an admitting department, a patient records department, a laboratory department, an insurance company, a pharmacist, an imaging system, and/or other actor(s). It is to be appreciated that such communication can occur before, during, and after a workflow has been implemented.

By way of example, in this instance the orchestrator 114 communicates billable scheduled appointments such as the scheduled imaging procedure, a laboratory test, a stress test, an ECG, etc., and completion thereof to the billing department. The billing department can use such information to automatically generates and send out invoices to the patient, the patient health care insurance provider, a third party, and/or other actor. The billing department may also use such communication to trigger re-sending of outstanding invoices, notify a collection agency, notify the orchestrator 114 and/or other actor about any outstanding invoices, update the status of an invoice, change the amount of an outstanding invoice, etc.

The orchestrator 114 may employ a set of rules in a rules bank to determine an appropriate action (including an action of no action) for the information received from the billing department. In one instance, the information invokes the orchestrator 114 to notify the patient regarding the outstanding invoice. Additionally or alternatively, the orchestrator 114 may notify a department schedule to run a test on the patient. The department may also remind the patient of the outstanding invoice. The department may also delay or cancel the scheduled procedure (depending, for example, on an urgency or importance of the procedure) until the invoice has been partially paid or paid in full.

FIGS. 2-8 describe the actors 102 in the context of an example healthcare imaging procedure workflow. Similar to FIG. 9, however, it is to be appreciated that the actors 102 may include actors for implementing other imaging and/or non-imaging healthcare workflows and/or non-healthcare workflows.

Figure 2:
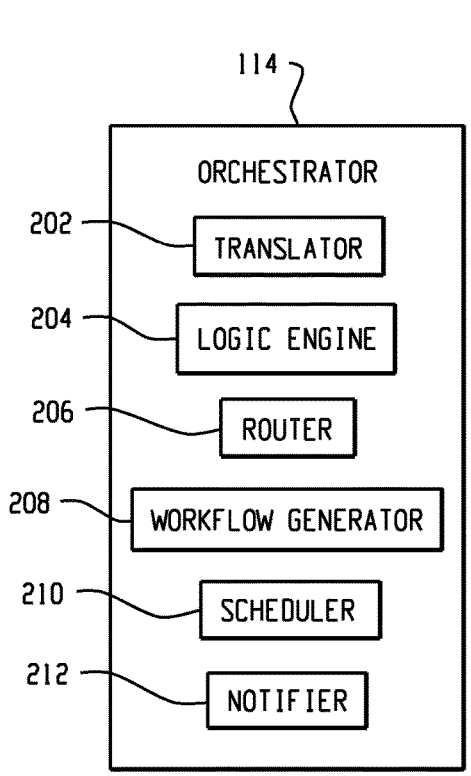
FIG. 2 illustrates an example orchestrator.

Referring to FIG. 2, the orchestrator 114 includes a translator 202, a logic engine 204, a router 206, a workflow generator 208, a scheduler 210, and a notifier 212, which can be implemented by the processor 116 executing instructions stored in the storage 118.

The translator 202 allows the orchestrator 114 to electronically communicate with the various different actors 102 configured to communicate using various different and/or non-compatible communication protocols. The translator 202 allows the orchestrator 114 to receive, read, write, repackage, reformat, send, and/or otherwise process data formatted in Digital Information Imaging and Communications in Medicine (DICOM), Health Level 7 (HL7), proprietary, and/or other formats.

The logic engine 204 responds to communication from one or more of the other actors 102. Such communication may include information related to retrieving or creating a patient record, obtaining stored and/or storing newly received healthcare information about the patient (e.g., image data, laboratory test results, family history, etc.), etc. Generally, the logic engine 204 is notified when information becomes available from one of the actors 102 and/or when one of the actors 102 can use information from the other actors 102.

The logic engine 204 invokes the router 206 to route data to and/or from the various actors 102. This may include facilitating retrieving information requested by one of the actors 102 from another one of the actors 102, such at the data repository 112, one of the machines 106, etc. This may also include sending data received from one of the actors 102 to one or more of the other actors 102, for example, from one of the machines 106 to one of the data processing devices 110.

The workflow generator 208 facilitates generating the workflow for a patient. The workflow may include the various acts to be performed, for example, from the scheduling of a patient for an imaging procedure to providing the results of the imaging procedure, including the radiologist report, to the referring clinician. Workflows can be stored in the data repository 112 and updated as the various acts of the workflow are completed and/or change.

The scheduler 210 facilitates scheduling the imaging procedure in the imaging workflow. In one instance, the scheduler 210 schedules an imaging procedure based on the availability of the patient, the scanner, the operator of the scanner, the radiologist reading the resulting images, the referring physician, and/or other information. The scheduler 210 can also be used to re-schedule an imaging procedure.

The notifier 212 notifies the various actors 102 of events related to the workflow. For example, once a schedule is created, the scheduler 210 can send the schedule and/or reminders to the relevant actors 102 using the various communication devices 120. The notifier 212 can also notify the actors 102 of any schedule changes and/or conflicts.

Figure 3:
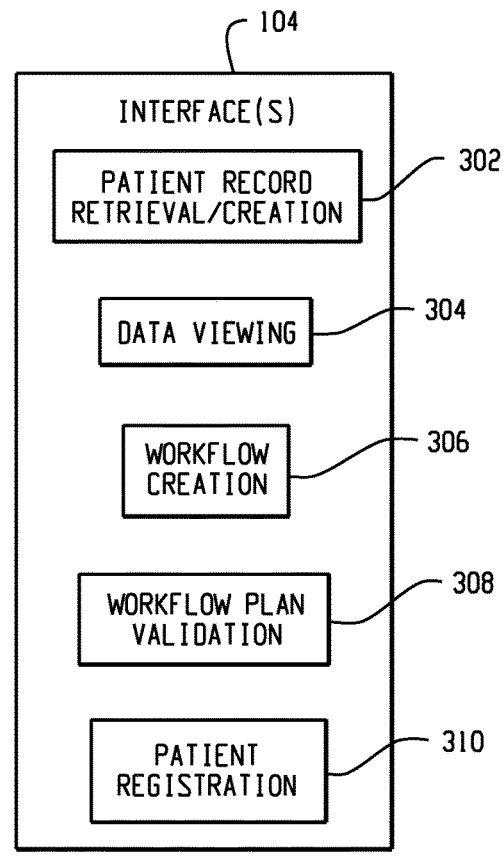
FIG. 3 illustrates an example interface(s).

Turning to FIG. 3, the user interfaces 104 includes a patient record retrieval/creation user interface 302. This interface can be employed by authorized healthcare personnel to identify a current patient of interest. This may include providing the patient's name, a unique identifier (UID) (e.g., patient social security number), and/or other patient information to the interface 302 via an input device such as a keyboard, a mouse, keypad, executing voice recognition software, a touch screen, etc.

The input information is provided to the orchestrator 114, which queries, via the router 206, the data repositories 112 for a patient record corresponding to the identified patient. Where a record is located, a confirmation signal and/or the patient record are presented via the patient record retrieval/creation user interface 302. Where a record for the patient is not found in the data repository, a message indicating this is presented via the patient record retrieval/creation user interface 302. In the latter case, the patient record retrieval/creation user interface 302 can be used to generate a record for the patient that is stored in the data repository 112.

The patient record retrieval/creation user interface 302 may be employed at a doctor's office, an admitting department at a health care facility, etc. As briefly noted above, the patient record retrieval/creation user interface 302 can be implemented as a web and/or console application.

A data viewing interface 304 allows the clinician to view healthcare information (e.g., images, reports, medical history, etc.) stored in the data repository 112 corresponding to the patient of the received or created record. The viewed information can be variously employed, for example, for facilitating determining whether the patient should undergo an imaging procedure(s) and which imaging procedure(s).

A workflow creation interface 306 facilitates generating an imaging workflow plan that includes the imaging procedure(s), in connection with the workflow generator 208.

A workflow validation interface 308 facilitates validating the imaging procedure(s) prior to the imaging procedure(s). This may entail determining whether another imaging procedure is more likely to provide information that is more useful. In one instance, a radiologist employs the workflow validation interface 308 to review the imaging procedure and either confirm or change the imaging procedure.

A patient registration interface 310 is used to log the patient in at the imaging department on the day of the imaging procedure.

Figure 4:
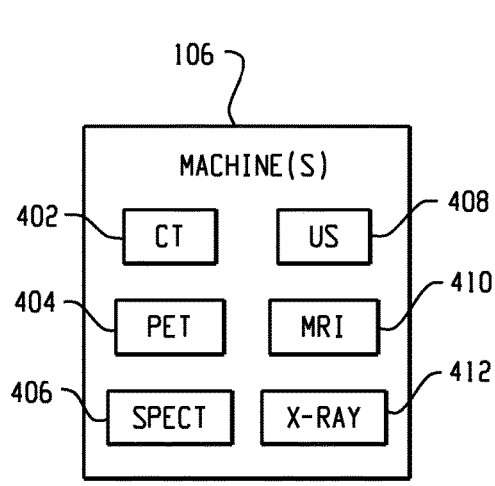
FIG. 4 illustrates an example machine(s).

Turning to FIG. 4, the machine(s) 106 includes various imaging scanners such as computer tomography (CT) 402, positron emission tomography (PET) 404, single photon emission tomography (SPECT) 406, ultrasound (US) 408, magnetic resonance imaging (MRI) 410, x-ray 412, and/or other scanners. The orchestrator 114 can communicate with the various scanners, determine their capabilities and availability based on an electronic calendar, load protocols, and/or otherwise communicate with the scanners. The machine(s) 106 may also include one or more non-imaging devices.

Figure 5:
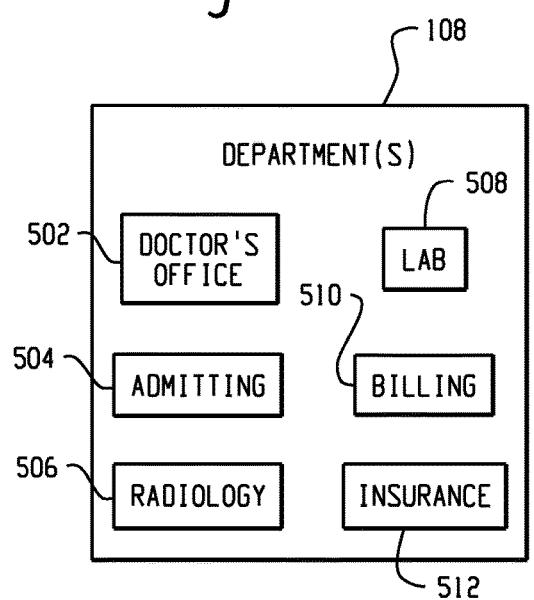
FIG. 5 illustrates an example department(s).

Turning to FIG. 5, the departments(s) 108 includes the various different departments that may contribute to the implementing the workflow. Examples of such departments include, but are not limited to, a doctor's office 502, an admitting department 504, a radiology department 506, a laboratory department 508, such as, for example, a pathology department, a billing department 510, an insurance department 512, etc.

Turning to FIG. 6, the data processing device(s) 110 includes various algorithms for processing data. Such processing may include processing imaging data based on the workflow plan, clinician preferences, etc. Examples of suitable processing algorithms include, but are not limited to, multi-planar reformatting (MPR) 602, maximum (or minimum) intensity projection (MIP) 604, 2D 606, 3D 608, 4D 610, segmentation 612, image registration/fusing 614, window/level 616, axial slices 618, sagittal slices 620, coronal slices 622, and/or other processing. The data processing device(s) may include a desktop computer or workstation computer with one or more processors and memory for variously processing the data.

Turning to FIG. 7, the communication device(s) 120 provide various types of communication including, but not limited to, pagers, cell phones, email, radio frequency identifications (RFID) tags, etc. The notifier 212 can use the various communication channels to notify relevant actors about the schedule, pre-imaging procedure acts (e.g., dietary constraints, ingestion of contrast agent, etc.), imaging procedure acts, post-imaging procedure, and/or other acts.

Turning to FIG. 8, the repository(s) 112 includes one or more sub-repositories, including imaging data repositories such as a picture archiving and communication system (PACS), a radiology information system (RIS), and/or the like, and non-imaging data repositories such as a hospital information system (HIS), an electronic medical record (EMR), and/of the like. Non-imaging data includes, but is not limited to, patient history, laboratory results, patient questionnaires, family history, and/or other non-imaging data. The repository(s) 112 also includes a workflow repository 814.

The above may be implemented by way of computer readable instructions, which when executed by a computer processor(s), cause the processor(s) to carry out the described acts. In such a case, the instructions are stored in a computer readable storage medium associated with or otherwise accessible to the relevant computer.

The invention has been described herein with reference to the various embodiments. Modifications and alterations may occur to others upon reading the description herein. It is intended that the invention be construed as including all such modifications and alterations insofar as they come within the scope of the appended claims or the equivalents thereof.

The invention claimed is:

1. A system, comprising:
 a plurality of processing actors, each including a computer processor, wherein the plurality of processing actors includes an imaging device from a group consisting of computed tomography, positron emission tomography, magnetic resonance imaging, ultrasound and X-ray; and
 an orchestrator, including a processor, configured to orchestrate closed-loop implementation of a workflow plan by the plurality of processing actors,
 wherein the processor:
  generates the workflow plan, in electronic format, based on an imaging procedure for a subject and the imaging device, wherein the workflow plan includes at least one action including performing the imaging procedure with the imaging device;
  creates a schedule, in electronic format, for the imaging procedure;
  conveys the schedule to at least one actor of the plurality of processing actors, wherein the at least one actor includes a computing device;
  transmits, in response to arrival of the scheduled date and over a network, a notification signal to the imaging device being used to perform the imaging procedure, wherein the notification signal causes the imaging device to load an identified imaging protocol for the imaging procedure to configure itself to scan the subject; and
  modifies the workflow plan to indicate the imaging procedure has been performed in response to completion of the imaging procedure, wherein the workflow plan includes at least one additional action to perform.

2. The system of claim 1, wherein the orchestrator orchestrates closed-loop implementation, wherein the closed-loop implementation includes workflow planning of an imaging procedure and providing an interpretation of one or more images resulting from the imaging procedure.

3. The system of claim 1, wherein the processor transmits a signal to a communication device of a user during the closed-loop implementation of the workflow plan, wherein the user is a patient and the at least one additional action notifies the patient to ingest contrast agent for the imaging procedure.

4. The system of claim 1, wherein the processor transmits a signal to a communication device of a user during the closed-loop implementation of the workflow plan, wherein the user is a radiologist and the at least one additional action notifies the radiologist that image data is available to read.

5. The system of claim 1, wherein the processor transmits a signal to a communication device of a user during the closed-loop implementation of the workflow plan, wherein the user is a referring physician and the at least one additional action notifies the referring physician that a radiologist report is available to review.

6. The system of claim 4, wherein the orchestrator extends the workflow plan to include another step based on a finding in a result of an imaging or non-imaging procedure.

7. The system of claim 1, wherein the processor transmits a signal to a communication device of a user during the closed-loop implementation of the workflow plan, wherein the user is a radiology technician and the at least one additional action notifies the radiology technician that a patient to be scanned has arrived is ready to scan.

8. The system of claim 4, wherein the orchestrator changes the workflow plan based on a change in an availability of one or more resources employed to implement the workflow plan.

9. The system of claim 1, wherein the orchestrator provides a web based application for communicating data between the orchestrator and the plurality of actors.

10. The system of claim 9, wherein the web based application is configured to receive an input indicative of an acceptance or a rejection of the predetermined plan by authorized personnel.

11. The system of claim 1, wherein the orchestrator facilitates transferring information between at least two of the plurality of actors employing non-compatible communication protocols.

12. The system of claim 1, wherein an actor queries the orchestrator for healthcare based information.

13. The system of claim 1, wherein an actor notifies the orchestrator when the actor has information available for at least one other actor.

14. The system of claim 13, wherein the information is automatically routed to the at least one other actor.

15. The system of claim 1, wherein at least one actor stores imaging workflow plans.

16. The system of claim 1, wherein at least one actor includes one or more data repositories.

17. The system of claim 16, wherein at least one of the data repositories stores non-imaging data.

18. The system of claim 16, wherein at least one of the data repositories stores imaging data.

19. The system of claim 1, wherein the imaging device receives proximity information from a hardware device carried by the subject and loads the identified imaging protocol in response to receiving the proximity information.

20. The system of claim 19, wherein the proximity information indicates the subject has already arrived for the imaging procedure.

21. The system of claim 1, wherein the notification signal identifies the imaging protocol to load to the imaging device.

22. The system of claim 1, wherein the processor receives proximity information from a hardware device carried by the subject and transmits the notification signal to the imaging device in response to receiving the proximity information.

23. A method for implementing a workflow plan for a patient via a processor of an orchestrator in communication with a plurality of processing actors that process sub-portions of the workflow plan via closed-loop orchestration, comprising:

creating and storing a schedule, in electronic format, for an imaging procedure of the healthcare workflow plan with an imaging device from a group consisting of computed tomography, positron emission tomography, magnetic resonance imaging, ultrasound and X-ray;

generating and transmitting, with a processor, a first signal to a communication device of a user during the closed-loop implementation of the workflow plan, wherein the first signal causes an action of the workflow plan to be performed by the communication device, the action is communication of proximity information, and the proximity information causes the imaging device to configure itself with an identified imaging protocol for the imaging procedure; and receiving, with the processor, a second signal indicating the action was performed; and modifying, with the processor, the healthcare workflow plan to indicate the action was performed.

* * * * *